United States Patent [19]

Hirota et al.

[11] Patent Number: 4,940,845

[45] Date of Patent: Jul. 10, 1990

[54] ESTERIFICATION PROCESS OF FATS AND OILS AND ENZYMATIC PREPARATION TO USE THEREIN

[75] Inventors: Yoshitaka Hirota; Yukitaka Tanaka; Kouichi Urata, all of Hasakimachi, Japan

[73] Assignee: Kao Corporation, Tokyo, Japan

[21] Appl. No.: 735,421

[22] Filed: May 17, 1985

[30] Foreign Application Priority Data

May 30, 1984 [JP] Japan ............................... 59-110333
May 30, 1984 [JP] Japan ............................... 59-110334

[51] Int. Cl.$^5$ ......................... C12P 7/64; C12N 9/20; C12N 11/14
[52] U.S. Cl. .................................. 435/134; 435/198; 435/176
[58] Field of Search ....................... 435/134, 198, 176

[56] References Cited

U.S. PATENT DOCUMENTS 4,268,527  5/1981  Matsuo et al. .................. 435/134 X
4,472,503  9/1984  Matsuo et al. ...................... 435/176

Primary Examiner—Elizabeth C. Weimar
Assistant Examiner—Charles L. Patterson
Attorney, Agent, or Firm—Flynn, Thiel, Boutell & Tanis

[57] ABSTRACT

The interesterification of fats and oils is effectively conducted in the presence of an enzymatic preparation which has an interesterification activity and has been prepared by adding fats and oils to a mixture of a lipase activator, a lipase and a carrier.

11 Claims, No Drawings

ESTERIFICATION PROCESS OF FATS AND OILS AND ENZYMATIC PREPARATION TO USE THEREIN

The invention relates to a process for interesterification of fats and oils with the use of an enzymatic preparation of a lipase.

The interesterification reaction of fats and oils is an important technique comparable to hydrogenation in the preparation of processed fats such as margarines and shortening oils.

The interesterification reaction of fats or oils has been carried out by a chemical technique using an alkaline substance such as an alkali metal alcoholate, an alkali metal or an alkali metal hydroxide as a catalyst. However, in this process, no specificity with respect to the position of the fatty acid in the resulting fat or oil is obtained at all, since the interesterification occurs without specificity of the position of fatty acid in the fat or oil. Thus, a defect of the conventional chemical interesterification process is non-selectivity with respect to the position of the fatty acid in the fat or oil.

Recently, processes for the interstification of fats or oils with position specificity have been proposed in place of the non-selective conventional process.

A typical example of these processes is one wherein a lipase which is an enzyme for the hydrolysis of fats and oils is used (see the specification of Japanese Patent Laid-Open No. 104506/1977).

In this process, it is an indispensable requisite that water be contained in the reaction system to activate the lipase. Though the water content is as low as only 0.2 to 1.0%, formation of diglycerides as the by-product of hydrolysis of the fats or oils and reduction in the yield of the exchange product cannot be avoided so long as a small amount of water is present in the reaction system, since lipase has an essential property of hydrolyzing fats and oils in the presence of water.

By-products such as diglycerides should be removed, since they damage the desirable properties of the interesterification product. Complicated purification steps are necessary for this removal. Thus, the conventional processes are unsatisfactory.

Under these circumstances, there have been proposed processes wherein the interesterification is conducted efficiently by controlling the hydrolysis of fats and oils by overcoming the defects of the known processes. They include the following processes:

(a) a process wherein a lower polyhydric alcohol is used in place of water as a lipase activator to inhibit the hydrolysis of the fat or oil in the interesterification reaction (Japanese patent B publication No. 6480/82 and Japanese patent A publication (unexamined) No. 78496/82), (b) a process developed on the basis that interesterification occurs at an interface between the oil and water (lipase is water-soluble) in a heterogeneous system; this process comprising adding a surfactant (emulsifier) to the heterogeneous reaction system to contact the fat or oil with lipase efficiently at the interface (specification of Japanese Patent Laid-Open No. 198798/1982), (c) a process wherein the interesterification rate is increased by controlling the water content with a water-absorptive resin capable of absorbing water in an amount several hundred times as much as its own weight (Japanese Patent Laid-Open No. 116689/1983), and (d) a process wherein the interesterification of the fat or oil is carried out by using an ester of a lower alcohol and a fatty acid having a low melting point in place of the fatty acid itself having a higher melting point to perform the reaction more uniformly (specification of Japanese Patent Publication No. 27159/1982).

Since, however, these known processes have defects as described below, they cannot be employed as satisfactory industrial processes. The defects are as follows:

The process (a) is characterized in that a lower polyhydric alcohol such as glycerol is used in place of water as a lipase activator. According to the inventors' investigations, however, it has been found that the interesterification rate is extremely low and a time of nearly one week is required for obtaining an intended conversion, though the hydrolysis reaction is controlled to some extent.

In the process (b), the oil can be contacted effectively with the lipase at the interface between the oil layer and the aqueous layer and the interesterification reaction proceeds selectively when the surfactant (emulsifier) is added thereto. It may be considered that an inverse micelle is formed on the surface of the enzyme protein to realize a condition suitable for the production of a complex of the lipase and the substrate and, as a result, a high interesterification activity is obtained.

However, as shown in the examples given in said specification, hydrolysis cannot be controlled sufficiently and the surfactant (emulsifier) remains in the interesterification product to damage the physical properties of the fat or oil. Therefore, the emulsifier should be removed from the product by a complicated procedure. Thus, this process is not a satisfactory industrial process.

In the process (c), the hydrolysis of the fat or oil cannot be controlled sufficiently and a starting monomer present as an impurity in the resin might be exuded and incorporated into the fat or oil. In the inventors' experiments conducted according to the process (c), the water-absorptive resin was swollen and adhered to the walls of the reactor when it was in contact with water. This invites loss of the lipase, which is disadvantageous in the recovery and reuse of the lipase.

In the process (d), the fatty acid ester must be prepared prior to the interesterification, inviting complication of the steps.

As described above, all of the known processes have several defects which hinder the industrial practice of them.

Though various other processes have been proposed, no process has been found for carrying out only the interesterification reaction while controlling the hydrolysis of the fat and oil.

Under these circumstances, the present inventors have conducted intensive investigations for the purpose of developing a process which allows only the intended interesterification to be carried out efficiently while controlling the hydrolysis of fats and oils, and have found that the purpose can be attained by using an enzymatic preparation obtained by a novel, easy lipase activation process. The present invention has been completed on the basis of this finding.

For the production of the active lipase, there has been proposed a process wherein a carrier is dispersed in an aqueous lipase solution to adsorb the lipase or a lipase-containing substance on the carrier and then the carrier is dried to obtain an enzymatic preparation having a given water content (see, for example, the specifications of Japanese Patent Laid-Open Nos. 127087/1981 and 48006/1983).

Since, however, these known processes have defects as described below, they cannot be employed as satisfactory industrial processes.

In the process for the interesterification of fat or oil using a very small amount of water as the enzyme activator, it has been pointed out that the hydrolysis of fats or oils occurs in addition to the intended interesterification and reduces the yield of the interesterification product [see, for example, "Journal of the American Oil Chemist's Society" Vol. 60, 291-294 (1983)]. According to the inventors' investigations, it has been found that when water used in said process is replaced with a lower polyhydric alcohol such as glycerol, the interesterification rate is extremely low and a period of time of nearly one week is required for obtaining an intended conversion, though the hydrolysis reaction is controlled to some extent.

By-products formed in the hydrolysis of the oil or fat damage the properties of the intended interesterification product and make the production of the product having a high quality or an intended quality impossible. Further, to keep the intended quality, the by-products should be removed by isolation and purification treatments in an additional step. This invites complication of the steps which is not preferred from the industrial viewpoint and, in addition, the composition of the fat or oil might be modified by said treatment.

Thus, the conventional processes wherein the enzyme activator is used were insufficient. Recently, the use of a surfactant (emulsifier) (see the specification of Japanese Patent Laid-Open No. 198798/1982) or a resin having a high water absorptivity (see the specification of Japanese Patent Laid-Open No. 116689/1983) have been proposed as a catalyst for an efficient enzymatic interesterification by overcoming the defects of the enzyme activator and controlling the hydrolysis. However, even when the enzyme catalysts are used according to these processes, hydrolysis cannot be inhibited sufficiently and the emulsifier may remain in the interesterified fat or impurities (such as monomers) contained in the resin of the high water absorptivity might be exuded. Therefore, these processes are also insufficient.

As for the second process, i.e. the preparation of the active enzyme, drying should be conducted for a long period of time to obtain the high enzymatic activity and the drying rate should be controlled strictly to obtain an optimum enzymatic activity. In addition, the enzymatic activity is reduced by the drying treatment conducted over a long period of time. Thus, this process is not a satisfactory industrial process, since it requires a complicated operation and much labor.

Under these circumstances, the present inventors have conducted intensive investigations on enzymatic catalysts which allow only the intended interesterification to be carried out efficiently while minimizing side reactions, and have found a process for producing an enzymatic preparation by a simple, novel enzyme activation technique. The present invention has been completed on the basis of this finding.

According to the instant invention, the interesterification of fats and oils is effectively conducted in the presence of an enzymatic preparation which has an interesterification activity and has been prepared by adding fats and oils to a mixture of a lipase activator, a lipase and a carrier. The esterification step is conducted further in the presence of a lipase activator.

The invention moreover provides a process for preparing the enzymatic preparation which comprises the steps of adding fats and oils to a mixture of a lipase activator, a lipase and a carrier, reacting them with each other to decompose the fats and oils and removing the fats and oils out of the decomposition product to separate the enzymatic preparation. The process also comprises the steps of adding oils and fats to a mixture of an enzyme activator, a lipase and a carrier, reacting them with each other to decompose the fats and oils and removing the fats and oils out of the decomposition product to separate the enzymatic preparation.

In addition, the invention provides the enzymatic preparation obtained by the process defined above.

According to the present invention, a lipase activator such as water or a dihydric or trihydric lower alcohol is added to a lipase, and a carrier and fats or oils are added to the mixture to decompose the fats or oils by the lipase and to realize the activity of the enzyme, whereby obtaining an enzymatic preparation having a high interesterification activity. By using the obtained enzyme (hereinafter referred to as "the enzymatic preparation"), the interesterification of the fats and oils can be effected efficiently while controlling the hydrolysis.

Recently, interesterification processes wherein an enzymatic preparation having a high activity obtained by adsorbing a lipase on a carrier is used have been developed (see, for example, the specifications of Japanese Patent Laid-Open Nos. 127094/1981 and 8787/1982).

However, in these known processes, a complicated operation is necessary for the production of the enzymatic preparation, since a long period of time is required for drying and the drying rate should be controlled strictly. As to interesterification with the enzymatic preparation, there has been disclosed a process wherein a reaction liquid is passed through a column packed with the enzymatic preparation and a process wherein a dehydrating agent is used in controlling the hydrolysis of the fat or oil or the reaction system is kept under reduced pressure. However, these processes cannot be performed easily on an industrial scale, since they necessitate complicated operations. Thus, the known processes are unsatisfactory.

The process of the present invention will now be described in detail.

A fat or oil is added to a mixture comprising a lipase activator, such as water or a dihydric or trihydric lower alcohol, a lipase and a carrier to react them with each other and to decompose the fat or oil. Then, the fat or oil is removed from the decomposition product by filtration or the like to obtain an enzymatic preparation. The obtained enzymatic preparation may be used in interesterification as it is or, if necessary, after washing with a solvent which does not damage the enzymatic activity, such as hydrocarbon, followed by drying.

The interesterification reaction is conducted by reacting a mixture comprising a fat or oil, a fatty acid and a solvent (a hydrocarbon) in the presence of the enzymatic preparation obtained as above or by reacting a fat or oil with a mixture comprising a fat or oil and a solvent (a hydrocarbon) in the presence of said preparation.

In the interesterification reaction carried out in the presence of the enzymatic preparation, a lipase activator, such as water or a dihydric or trihydric lower alcohol, may be used, if necessary, though the purpose can be attained sufficiently in the absence of any lipase activator. A purified interesterification product can be obtained by removing the fatty acid and small amounts of monoglyceride and diglyceride from the interesterification product by a known separation and purification method such as liquid-liquid extraction, neutralization with an alkali, vacuum distillation or molecular distillation.

The lipase used in the present invention has preferably a specific selectivity such as a selectivity for a position of glyceride to be bonded or a selectivity for a variety of the fatty acids, since when the selectivity is poor in the enzymatic interesterification, no special superiority to the conventional interesterification process wherein an alkali metal catalyst or the like is used can be obtained. The lipases having an excellent position selectivity include, for example, those produced by microorganisms of Rhizopus, Aspergillus, Candida and Mucor and pancreas lipase. In the specific interesterification of fatty acid groups in positions 1 and 3 of a glyceride, a lipase produced by *Rhizopus delemar*, *Rhizopus japonicus* or *Mucor japonicus* is suitable. These lipases are available on the market.

Preferred enzyme activators are water and dihydric and trihydric lower alcohols. Among them, water and glycerol are particularly effective.

The carrier may be selected from among known carriers. The useful carriers are those insoluble in the reaction system used in the production of the enzymatic preparation and the interesterification reaction of the invention that do not damage the enzymatic activity. They include, for example, Celite, diatomaceous earth, kaolinite, perlite, silica gel, glass fibers, active carbon, cellulose powder and calcium carbonate. The carrier may be in the form of a powder, granules, fibers, etc.

The fats and oils used in the present invention include ordinary vegetable and animal fats and oils as well as processed fats and oils and mixtures of them. Examples of them include soybean oil, cotton seed oil, rape oil, olive oil, corn oil, coconut oil, safflower oil, beef tallow, lard and fish oils. In the production of a substitute for cocoa butter by the interesterification, there may be used fats and oils containing a large amount of oleic acid in position 2 of glycerol, such as palm fat, olive oil, tsubaki oil, sasanqua oil, sal fat, illippe butter, kokum butter, shea butter, mowrah fat, phulwara butter, borneo tallow and those fractionated from them. Though fat or oil used for the production of the enzymatic preparation may be selected independently from fat or oil used in the interesterification, it is desirable that a fat or oil having a composition close to that of fats or oils used in the interesterification reaction is used in the production of the enzymatic preparation.

The interesterification of the fat or oil is conducted by reacting it with a fatty acid or by reacting it with a fat or oil.

The fatty acids are straight-chain fatty acids having 8 to 22 carbon atoms and occurring in nature, such as palmitic, stearic, or oleic acid.

In the interesterification, reaction alcohol esters of fatty acids may be used in addition to the above-mentioned fatty acids. The alcohol/fatty acid esters include those obtained from the above-mentioned fatty acids (straight-chain fatty acids having 8 to 22 carbon atoms) and saturated straight-chain monohydric alcohols. For example, there may be mentioned methyl palmitate, ethyl palmitate, methyl stearate and ethyl stearate. The fat or oil may be selected according to the purpose from the above-mentioned ones, i.e. ordinary vegetable fats and oils, animal fats and oils, processed fats and oils and mixtures of them.

The solvents used in the interesterification reaction according to the present invention are organic solvents inert to lipases. Examples of them include n-hexane, commercial hexane, petroleum ether and petroleum benzine. A solvent used in the interesterification may be used also in the production of the enzymatic preparation.

The process of the present invention will now be described in detail.

An enzymatic preparation is prepared from a fat or oil, a lipase activator (water or a dihydric or trihydric lower alcohol), a lipase and a carrier. More particularly, 0.01 to 10 parts by weight of a commercially available lipase, 0.1 to 20 parts by weight of a lipase activator and 1 to 50 parts by weight of a carrier are added to 100 parts by weight of a fat or oil. They are then stirred at 20° to 80° C. for 1 to 24 hours to decompose the fat or oil. The decomposition of the fat or oil is conducted in the above-mentioned temperature range and desirably at a temperature most suitable for the lipase. Then, the fat or oil is removed from the decomposition product by filtration or the like to obtain the intended enzymatic preparation. The enzymatic preparation may be used as is in the interesterification reaction. If necessary, the enzymatic preparation may be washed with an inert organic solvent which does not damage the activity of the enzyme such as the above-mentioned hydrocarbons, e.g., n-hexane or petroleum benzine and then dried (drying by heating is not preferred, since the enzyme activity is damaged by this treatment).

The interesterification reaction is conducted in the presence of the obtained enzymatic preparation as follows: a mixture of 100 parts by weight of a fat or oil, 25 to 300 parts by weight of a fatty acid (or an alcohol ester of fatty acid or another fat or oil), 0.1 to 100 parts by weight of the enzymatic preparation obtained as above (comprising 0.01 to 10 parts by weight of a lipase and a carrier), 0 to 10 parts by weight of water or a dihydric or trihydric lower alcohol as the lipase activator and, if necessary, 0 to 1000 parts by weight of an inert organic solvent is stirred at 20° to 80° C. The interesterification reaction according to the present invention may be carried out in said temperature range and preferably at a temperature suitable for the lipase. The reaction time is 1 to 3 days.

After completion of the interesterification reaction, the fatty acid and small amounts of monoglyceride and diglyceride can be removed easily from the reaction liquid by conventional isolation and purification means such as liquid-liquid extraction, neutralization with an alkali or vacuum or molecular distillation or a suitable combination of these means. Thus, the intended purified, interesterified product can be obtained.

The effects or advantages of the present invention reside in that the intended interesterification reaction of fat or oil can be carried out efficiently while controlling the hydrolysis thereof by using the enzymatic preparation having a high interesterification activity obtained by the easy process of the present invention. Thus, a process having a high productivity is provided.

Another effect of the invention is that deactivation of the enzyme by the reaction is insignificant and the enzymatic preparation recovered after completion of the reaction can be used again effectively. When the process is carried out on an industrial scale, its economical advantage is increased.

Further, by carrying out the interesterification reaction according to the present invention, for example, a highly valuable substitute for cocoa butter can be produced from inexpensive palm oil effectively by using a lipase having a special position selectivity.

The following examples and comparative examples will further illustrate the invention.

EXAMPLE 1

50 g of a soft fraction of palm oil, 5 g of Celite, 0.5 g of ion-exchanged water and 0.1 g of a commercially available lipase (lipase produced by *Rhizopus delemar*; a product of Seikagaku Kogyo Co.) were stirred together at 40° C. in a closed vessel for 12 hours to carry out an enzymatic reaction (hydrolysis). After completion of the reaction, an insoluble matter (mixture of Celite and lipase) was separated by filtration. It was washed with 5 ml of n-hexane three times to completely remove the oil. The product was then dried at 20° to 30° C. under reduced pressure for 1 h to obtain an enzymatic preparation.

2.6 g of the obtained enzymatic preparation (comprising 0.05 g of lipase and 2.55 g of Celite) was stirred together with 10 g of a medium melting point fraction of palm oil having an iodine value (IV) of 34 and a diglyceride content of 2%, 10 g of stearic acid and 40 ml of n-hexane at 40° C. in a closed vessel for 3 days to carry out the enzymatic reaction (interesterification reaction). After completion of the reaction, the conversion in the interesterification reaction was determined from a stearic acid content of the obtained oil and a diglyceride content (DG) was determined according to column chromatography. The results are shown in Table 1.

EXAMPLE 2

1 g of the enzymatic preparation obtained in Example 1 was stirred together with 10 g of a medium melting point fraction of palm oil (having an IV of 34 and a diglyceride content of 2%), 10 g of stearic acid, 0.015 g of ion-exchanged water and 40 ml of n-hexane at 40° C. in a closed vessel for 2 days to carry out the enzymatic reaction (interesterification reaction). After completion of the reaction, the conversion and diglyceride content were determined in the same manner as in Example 1 to obtain the results shown in Table 1.

COMPARATIVE EXAMPLE 1

The same procedure was repeated under the same reaction conditions (temperature and time) as in Example 1 except that the soft fraction of palm oil was replaced with 40 ml of n-hexane and the quantity of ion-exchanged water was altered to 0.09 g to obtain an enzymatic preparation. This product was isolated and 10 g of a medium melting point fraction of palm oil (having an IV of 34 and a diglyceride content of 2%) and 10 g of stearic acid were added thereto. The enzymatic reaction (interesterification reaction) was carried out at 40° C. in a closed vessel for 4 days.

After completion of the reaction, the conversion and diglyceride content were determined in the same manner as in Example 1 to obtain the results shown in Table 1.

COMPARATIVE EXAMPLE 2

20 mg of the same lipase as in Example 1 was stirred together with 10 g of a medium melting point fraction of palm oil (having an IV of 34 and a diglyceride content of 2%), 10 g of stearic acid, 0.018 g of ion-exchanged water and 40 ml of n-hexane at 40° C. in a closed vessel for 3 days to carry out the enzymatic reaction (interesterification reaction). After completion of the reaction, the conversion and diglyceride content were determined in the same manner as in Example 1 to obtain the results shown in Table 1.

TABLE 1

| Enzymatic preparation | Interesterification conditions Water content* | Reaction time | Conversion | Diglyceride content |
|---|---|---|---|---|
| Enzymatic preparation (Example 1) | —** | 3 days | 95% | 2.5% |
| Enzymatic preparation (Example 2) | 0.15 weight % | 2 | 96 | 4.0 |
| Enzyme prepared without using fat or oil (Comparative Example 1) | 0.18 | 4 | 6 | 7 |
| Commercially available enzyme without any treatment (Comparative Example 2) | 0.18 | 3 | 50 | 7 |

Note
*based on the fat or oil
**Ion-exchanged water was not used.

EXAMPLE 3

50 g of a soft fraction of palm oil was stirred together with 5 g of Celite, 0.5 g of glycerol and 0.1 g of a commercially available lipase (lipase produced by *Rhizopus delemar*; a product of Seikagaku Kogyo Co.) at 40° C. in a closed vessel for 12 h to carry out the enzymatic reaction (hydrolysis).

After completion of the reaction, an insoluble matter (mixture of Celite and lipase) was separated by filtration and then washed with 5 ml of n-hexane three times to remove the oil. After drying at 20° to 30° C. under reduced pressure for 1 h, an enzymatic preparation was obtained.

2.6 g of the obtained enzymatic preparation was stirred together with 10 g of a medium melting point fraction of palm oil (having an IV of 34 and a diglyceride content of 2%), 10 g of stearic acid and 40 ml of n-hexane at 40° C. in a closed vessel for 3 days to carry out the enzymatic reaction (interesterification reaction).

After completion of the reaction, the conversion in the interesterification reaction, determined from the stearic acid content of the obtained oil, was 95% and the diglyceride content of the obtained oil was 3.0%.

The embodiments of the invention in which an exclusive property or privilege is claimed are defined as follows:

1. A process for the interesterification of fats or oils comprising the steps of:
   (1) forming a mixture of a lipase, a carrier and a lipase activator selected from the group consisting of water, a dihydric lower alcohol and a trihydric lower alcohol;
   (2) adding a fat or oil to said mixture and conducting hydrolysis of said fat or oil in order to form a hydrolysis product mixture comprising said lipase immobilized on said carrier, a decomposition product of said fat or oil and unhydrolyzed fat or oil;
   (3) separating said unhydrolyzed fat or oil from said hydrolysis product mixture in order to form an enzymatic preparation;
   (4) forming a second mixture comprising said enzymatic preparation, a fat or oil, a compound having a fatty acid moiety to be added to said fat or oil, and a solvent and interesterifying said fat or oil; and (5) separating an interesterified product of said fat or oil from said second mixture.

2. A process as claimed in claim 1, in which said interesterification of said fat or oil is conducted further in the presence of a lipase activator.

3. A process as claimed in claim 2, in which said lipase activator is selected from the group consisting of water, a dihydric lower alcohol and a trihydric lower alcohol.

4. The process of claim 1, wherein said lipase activator is water or glycerol.

5. The process of claim 1, wherein said lipase is produced by *Rhizopus delemar*.

6. The process of claim 1, wherein an oil is interesterified.

7. The process of claim 6, wherein said oil is palm oil.

8. The process of claim 1, wherein said carrier is diatomaceous earth.

9. A process for preparing an enzymatic preparation comprising the steps of:
   (1) forming a mixture consisting essentially of a lipase, a carrier and a lipase activator selected from the group consisting of water, a dihydric lower alcohol and a trihydric lower alcohol;
   (2) adding a fat or oil to said mixture and conducting hydrolysis of said fat or oil to form a hydrolysis product mixture comprising said lipase immobilized on said carrier, a decomposition product of said fat or oil and unhydrolyzed fat or oil; and
   (3) separating said unhydrolyzed fat or oil from said hydrolysis product mixture in order to form said enzymatic preparation.

10. An enzymatic preparation prepared by the process of claim 9.

11. A process for the interesterification of palm oil comprising the steps of:
   (1) forming a mixture consisting essentially of a lipase produced by *Rhizopus delemar*, diatomaceous earth and water;
   (2) adding palm oil to said mixture and conducting hydrolysis of said palm oil in order to form a hydrolysis product mixture comprising said lipase immobilized on said diatomaceous earth, a decomposition product of said palm oil and unhydrolyzed palm oil;
   (3) separating said unhydrolyzed palm oil from said hydrolysis product mixture in order to form an enzymatic preparation;
   (4) forming a second mixture comprising said enzymatic preparation, palm oil, stearic acid and n-hexane and interesterifying said palm oil; and
   (5) separating an interesterified product of palm oil from the second mixture.

* * * * *